United States Patent [19]
Weyrauch et al.

[11] Patent Number: 5,296,911
[45] Date of Patent: Mar. 22, 1994

[54] OPTICAL TEST SYSTEM FOR A CHEMICAL ANALYZER

[75] Inventors: Bruce Weyrauch, Newman Lake; James Clark, Spokane; Norman Kelln, Spokane; Leon Schmidt, Spokane, all of Wash.

[73] Assignee: Schiapparelli Biosystems, Inc., Fairfield, N.J.

[21] Appl. No.: 916,193

[22] Filed: Jul. 16, 1992

[51] Int. Cl.$^5$ .................. G01N 21/00; G01N 21/25; G01J 3/28
[52] U.S. Cl. ..................... 356/73; 356/328; 356/417
[58] Field of Search ............. 356/73, 328, 368, 417, 356/418

[56] References Cited

U.S. PATENT DOCUMENTS

| | | | |
|---|---|---|---|
| 4,269,511 | 5/1981 | Erwin | 356/368 |
| 4,516,856 | 5/1985 | Popelka | 356/368 |
| 4,558,946 | 12/1985 | Galle et al. | 356/73 |
| 4,573,195 | 2/1986 | de France | 356/417 X |
| 4,730,922 | 3/1988 | Bach et al. | 356/73 |
| 4,786,169 | 11/1988 | Brierley et al. | 356/244 |
| 4,795,255 | 1/1989 | Kajzar et al. | 356/318 |
| 5,061,076 | 10/1991 | Hurley | 356/417 |

OTHER PUBLICATIONS

Schmidt, "A High-Performance Dual-Wavelength Spectrophotometer and Fluorometer", Journal of Biochemical and Biophysical Methods, v. 2 No. 3 180, pp. 171–181.

*Primary Examiner*—Robert J. Warden
*Assistant Examiner*—Chirstoher Y. Kim
*Attorney, Agent, or Firm*—Wells, St. John, Roberts, Gregory & Matkin

[57] ABSTRACT

A compact optical test system for a chemical analyzer comprises a light-proof enclosure formed by two joined side compartments. One includes control surfaces for accurately positioning optical elements along desired light paths. The other includes retaining surfaces to maintain the optical elements in a centered position across the parting line of the two compartments. A single light source is used for both absorbance and fluorescence polarization measurement purposes.

7 Claims, 17 Drawing Sheets

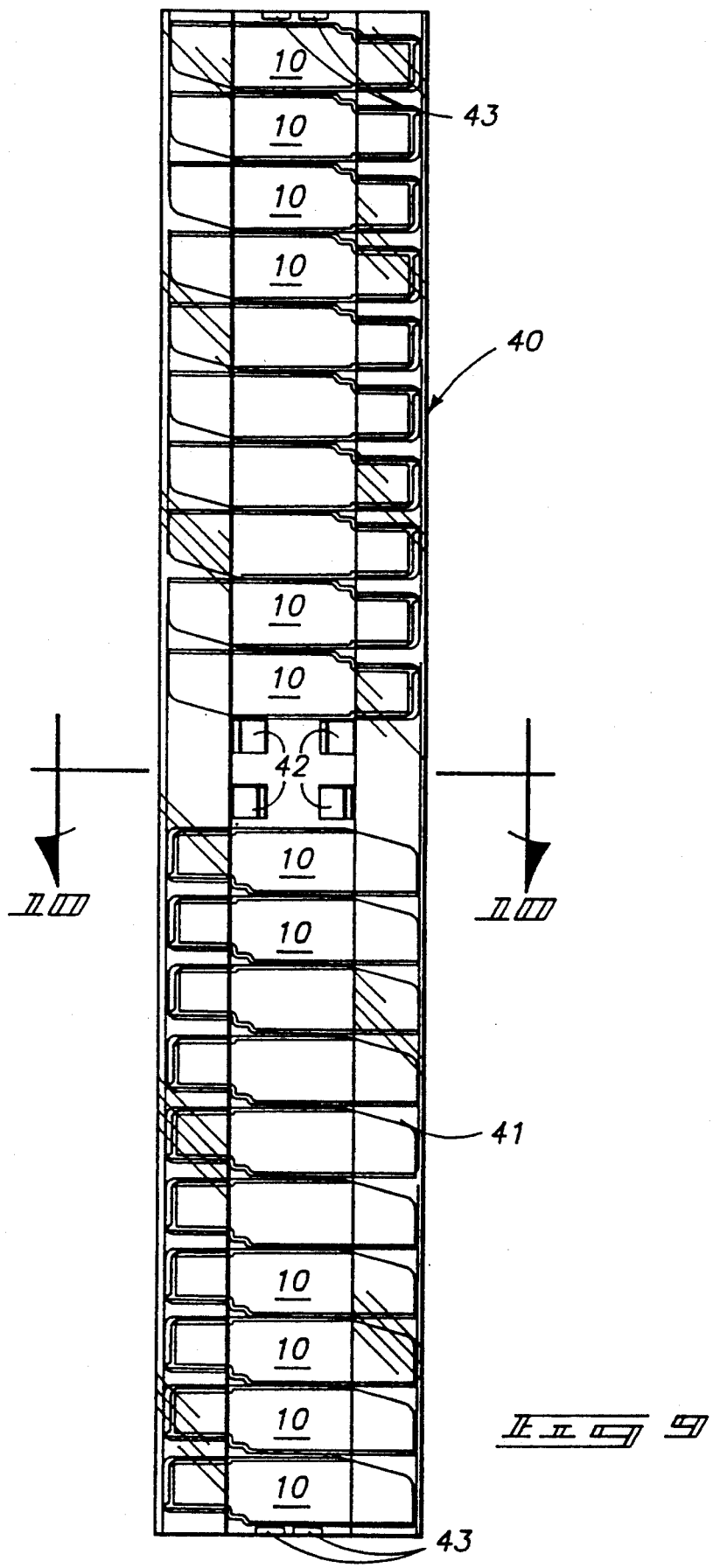

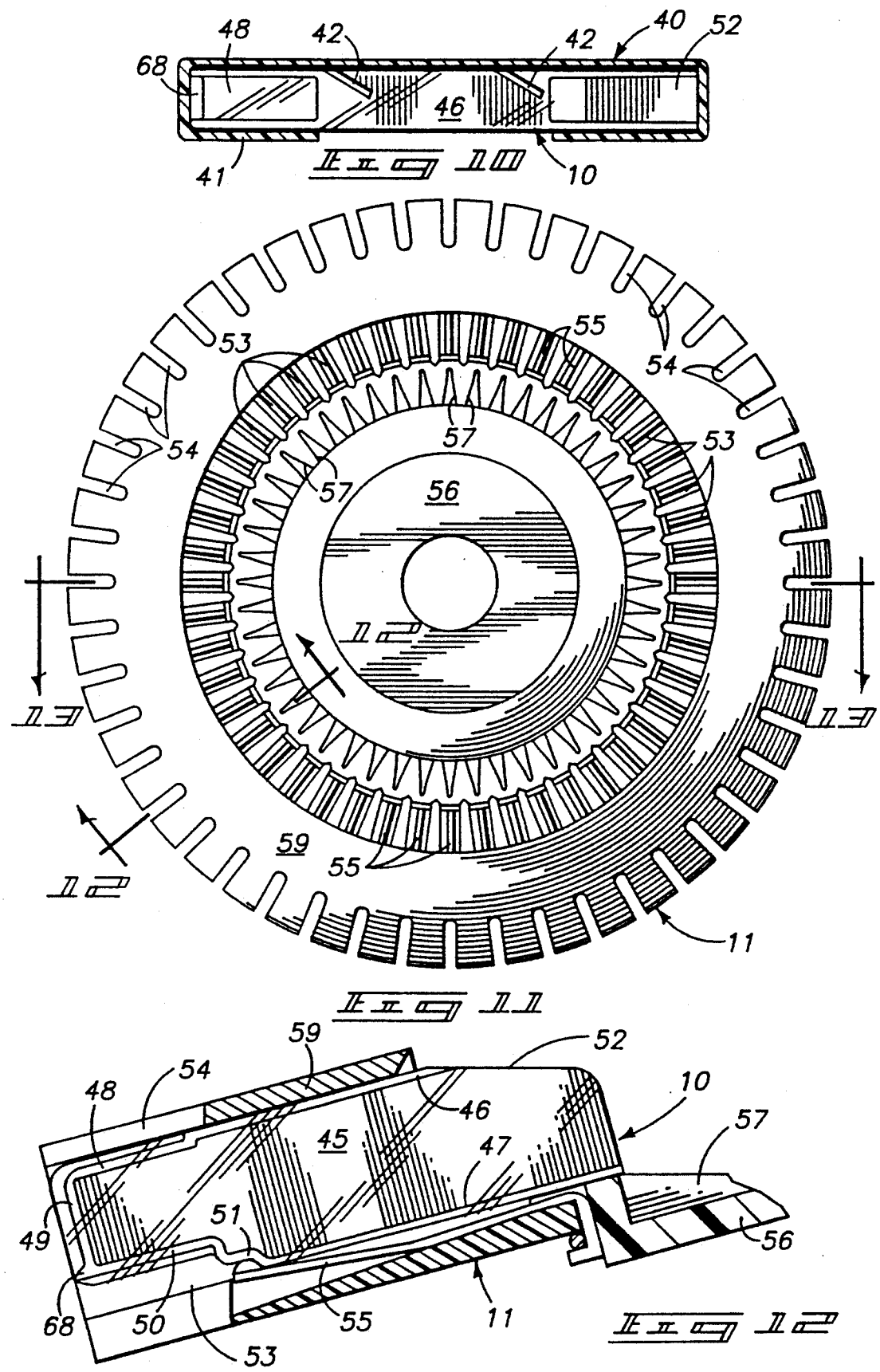

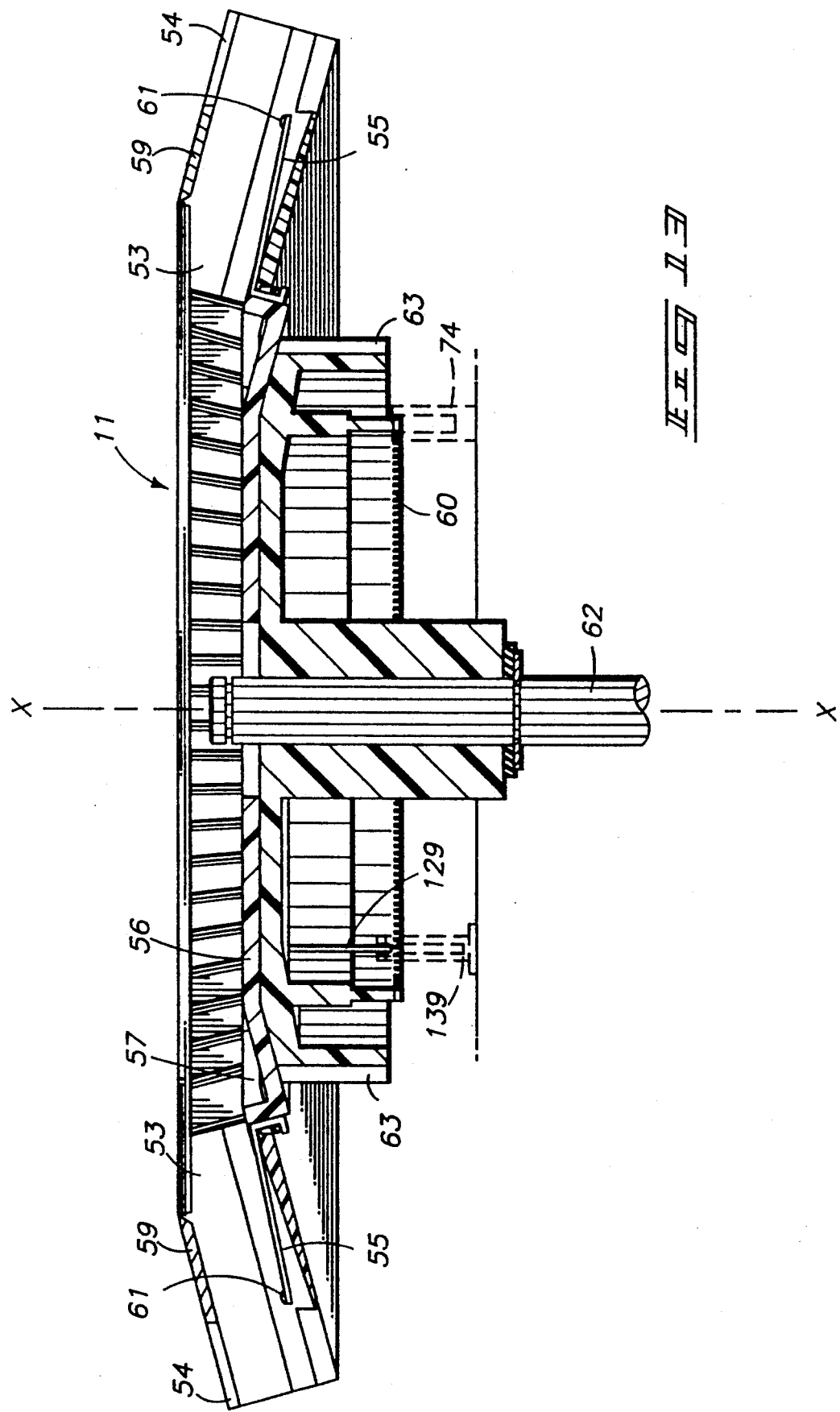

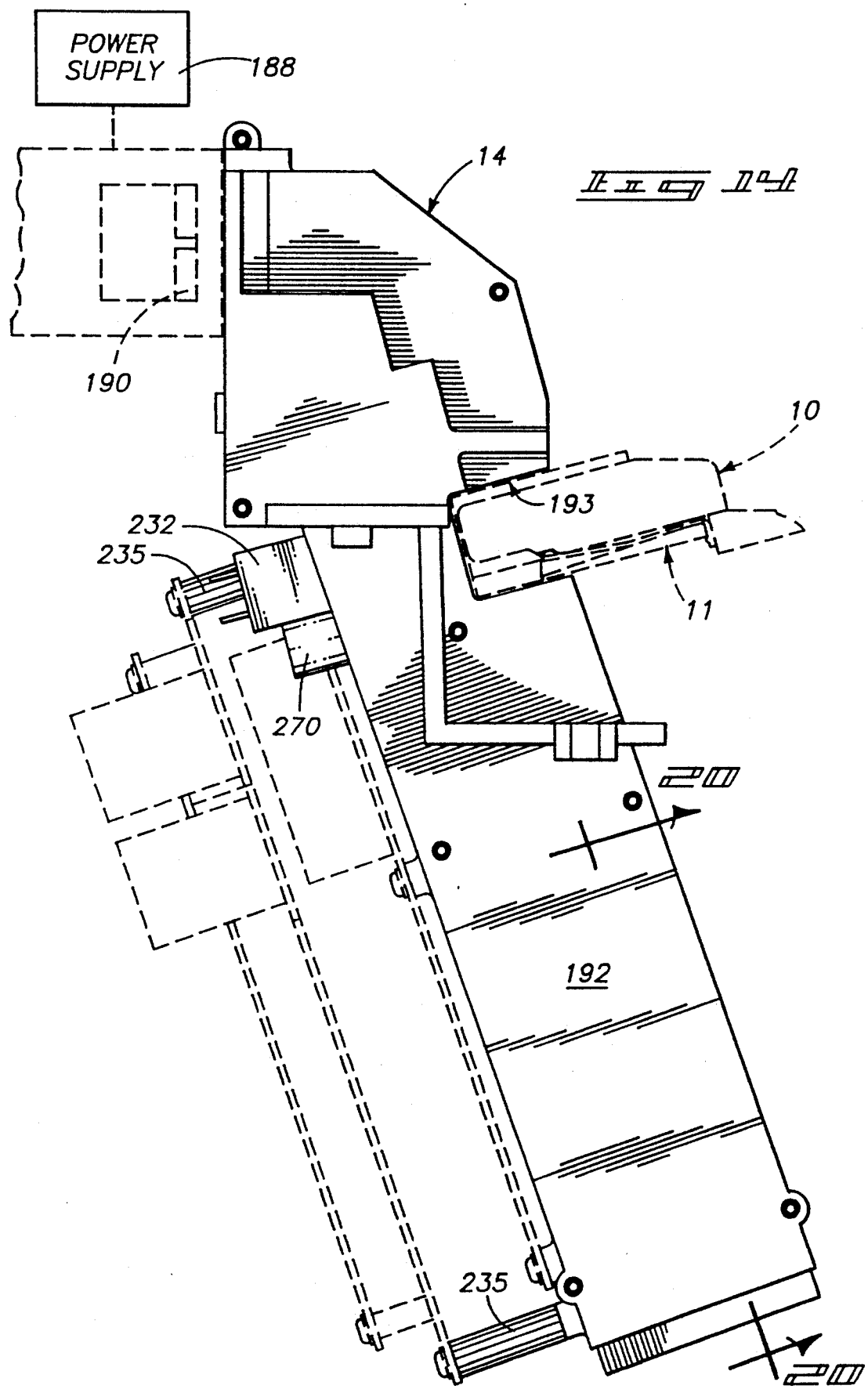

| TURNTABLE 11 | STATIONARY | MIX | ACCEL-ERATE | SPIN | DECEL-ERATE |
|---|---|---|---|---|---|
| PROBE ARM 17 | DISPENSE FLUID | WASH (SHORT) | | | |
| MAGAZINE 75 | INSERT CUVETTE | | | | |
| OPTICAL SYSTEM 14 | MOVE FILTER OUT | TRANSMIT DATA | | ABSORBANCE READINGS | MOVE FILTER IN | FLOUR-ESCENCE READINGS |

FIG. 22

OPTICAL TEST SYSTEM FOR A CHEMICAL ANALYZER

TECHNICAL FIELD

The disclosure pertains to an optical test system for inclusion within a clinical chemistry analyzer for testing of patient samples, such as blood or urine. It generally relates to automatic chemical analyzers for directly measuring properties of reacted liquids by photometric systems to determine optical absorbency and/or fluorescence of samples, thus producing qualitative and quantitative analyses of tested samples.

BACKGROUND OF THE INVENTION

Automated analyzers have been developed for biochemical analysis of patient samples, such as whole blood, serum, urine, plasma and cerebral spinal fluid. Most such equipment available today is large, complicated to operate, and high in cost.

The operation of such equipment is technically complicated. It typically requires specialized operators to be available at all times, with commensurate personnel expenses being encountered. It is usually designed for use by large laboratories serving a wide geographic area or by a large medical facility. These existing analyzers carry out tests in a defined sequence of operations designed for efficient, high volume usage.

Such large scale capacity is not always required, particularly in smaller medical clinics where large volumes of blood samples are not encountered on a daily basis. The present chemical analyzer was developed to meet the practical needs of smaller medical settings. It is designed as a desk-top unit that can be operated without specialized laboratory training. Its throughput is adequate for meeting typical clinical applications. As an example, it can be designed to produce a maximum of 164 test results per hour for routine, single reagent chemistries.

To provide a representative wide number of reagents, the analyzer has been designed to have a capacity of 40 reagent containers of two different sizes on board. Its capacity can be effectively doubled by utilizing two of the chemistry instruments in tandem, both being controlled by a common workstation.

The compact nature of the analyzer can be partially attributed to the fact that a single probe arm and pipette service all of the functional liquid-handling components included within it. The common pipette is used for transferring samples and reagents, as well as for diluting liquids as needed by particular test requirements.

To obtain large volumes of tests, conventional laboratory analyzers are programmed to conduct test procedures in a fixed sequence of events. While predetermined test sequences are practical in high volume chemical analyzer applications, there is a need for more flexible operation when scaling such test procedures to meet the needs of smaller medical facilities.

The present invention provides testing flexibility by permitting random access to each cuvette on a test turntable and to each container (cups, wells and reagent bottles) on a sample/reagent tray. It is therefore not necessary for the instrument to sequence through any predetermined processing steps—the controlling software can tailor the required steps to the tests currently requisitioned. This permits a greater number of tests to be conducted while using a minimum number of containers, cuvettes and reagent bottles. The software controls the sequencing of tests based upon predetermined priority schedules, rather than defined test sequences dictated by the nature of the tests being conducted.

Most existing analyzers are limited to accomplishing either photometric tests or potentiometric tests, but not both. The present chemistry analyzer, designed about a photometric testing system, has the capability of servicing a second analytical system, such as a potentiometric system. A single liquid transfer system provides samples to both analytical systems. Their results are controlled and computed by a common workstation.

A reaction turntable is capable of handling a maximum of 48 cuvettes at any given time. Both fluorescence polarization and absorbance tests can be carried out with respect to selected cuvettes through use of a single optical system.

Further details concerning the system will be evident from the following description.

BRIEF DESCRIPTION OF THE DRAWINGS

The preferred embodiment of the invention is illustrated in the accompanying drawings, in which:

FIG. 9 is a front elevation view of a loaded cuvette cartridge;

FIG. 10 is a transverse sectional view through a loaded cartridge as seen along line 10—10 in FIG. 9;

FIG. 11 is a plan view of the cuvette turntable;

FIG. 12 is an enlarged sectional view taken along line 12—12 in FIG. 11;

FIG. 13 is a transverse sectional view through the turntable as seen along line 13—13 in FIG. 11;

FIG. 14 is a side elevation view of the optical system enclosure;

FIG. 22 is a timing diagram of the instrument components.

DETAILED DESCRIPTION OF THE PREFERRED EMBODIMENT

Figure 1:
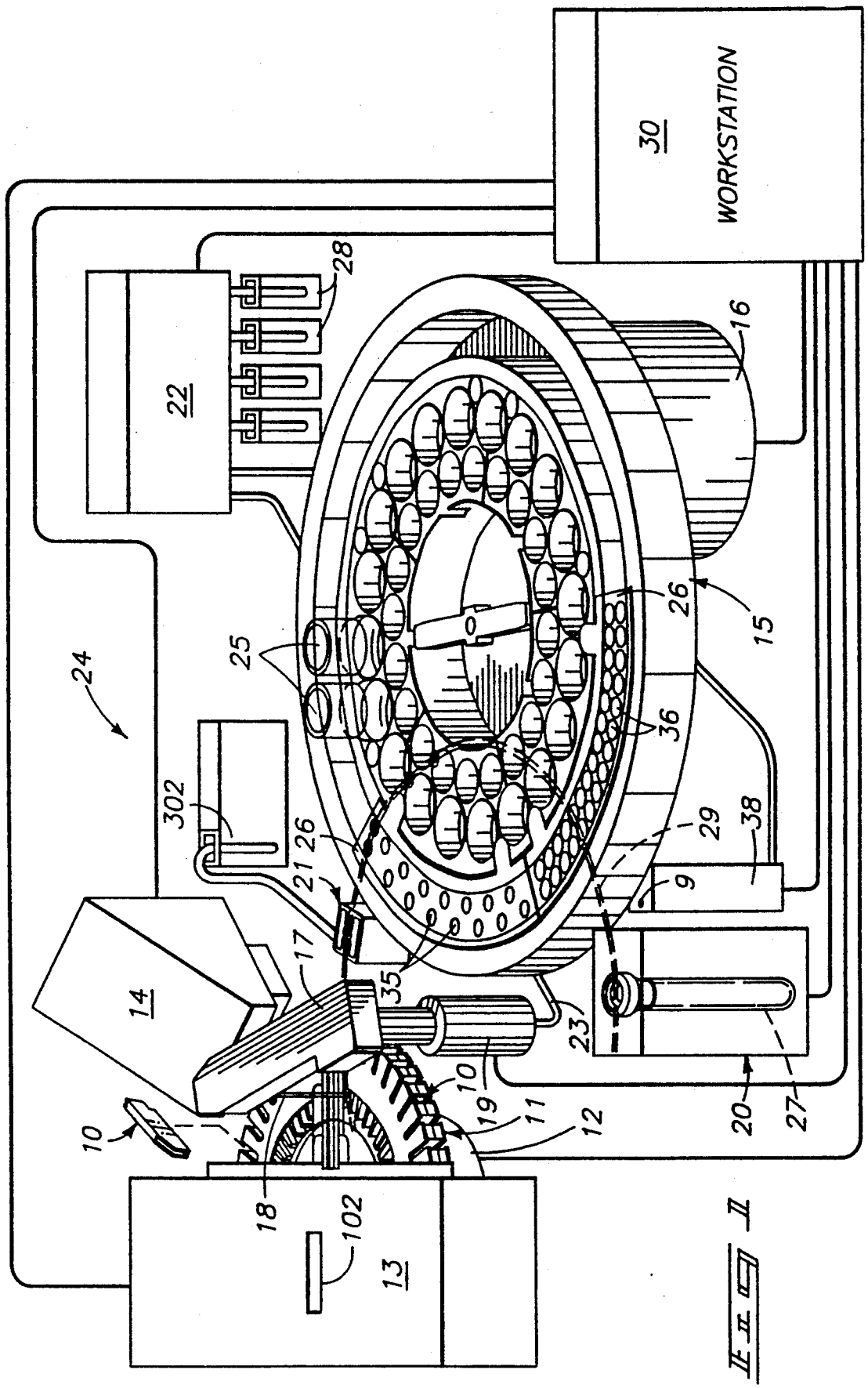
FIG. 1 is a diagrammatic perspective view of the principal components in the analyzer.

This disclosure of the invention is submitted in furtherance of the constitutional purposes of the U.S. Patent Laws "to promote the progress of science and useful arts" (Article 1, Section 8).

SYSTEM OVERVIEW

The automatic chemical analyzer (generally illustrated in FIGS. 1-3) includes a turntable 11 rotatably mounted about a first vertical axis. A plurality of disposable cuvettes 10 are releasably mounted to the turntable 11. A first power means, shown as motor 12, is operably connected to turntable 11 for alternately (1) indexing it at a stationary angular position about the first axis with a selected cuvette 10 positioned at a cuvette access station A or (2) turning it about the first axis while mixing or centrifuging contents of cuvettes mounted to it.

First analytical means, illustrated as an optical system 14, is provided adjacent to the turntable 11 for performing tests on the contents of the cuvettes 10 as they rotate about the turntable axis.

A tray 15 is rotatably mounted about a second vertical axis parallel to and spaced from the first axis. A plurality of containers 25, 35, and 36 are positioned about tray 15 for reception of samples and reagent liquids. Second power means, illustrated as motor 16, is operably connected to the tray 15. The motor 16 indexes tray 15 to a stationary angular position about the second axis with a selected container positioned at a container access station C.

The analyzer also includes a probe arm 17 movable about a third vertical axis parallel to the first axis. Probe arm 17 supports a downwardly-extending open pipette 18. The vertical pipette 18 is movable along an arcuate path centered about the third axis and intersecting both the cuvette access station A and container access station C. It can move along the arcuate path in a random fashion to transfer liquid from a container positioned on the tray at the container access station C to a cuvette 10 positioned on the turntable 11 at the cuvette access station A. The arcuate path of the pipette 18 can be visualized along a protective groove 29 formed at the exterior of the enclosure 39 housing the chemistry instrument 24.

The illustrated embodiment of the clinical chemistry analyzer consists of two major components: a chemistry instrument 24 and a workstation 30. The chemical instrument accepts liquid patient samples for testing purposes, performs appropriate optical and/or potentiometric measurements on the samples, and communicates the resulting test data to workstation 30. Workstation 30 is used by the operator to enter data, control operation of instrument components, accept data generated by the instrument, manage and maintain system information, and generate visual and printed reports about assays and instrument performance.

The chemistry instrument 24 is a separate unit with minimal operator controls. Either one or two identical chemistry instruments 24 can be linked to a single workstation 30, as required in a particular setting. The chemistry instrument 24 can perform several types of analysis. These include routine chemistries, electrolytes, therapeutic drug monitoring, drugs of abuse in urine, and other specialized tests.

The liquid-handling components that make up the chemistry instrument 24 are housed within enclosure 39 (FIGS. 2-5). It separates along a peripheral parting line 37 defining a lower supporting base 33 and an upper hinged cover 34.

Figure 2:
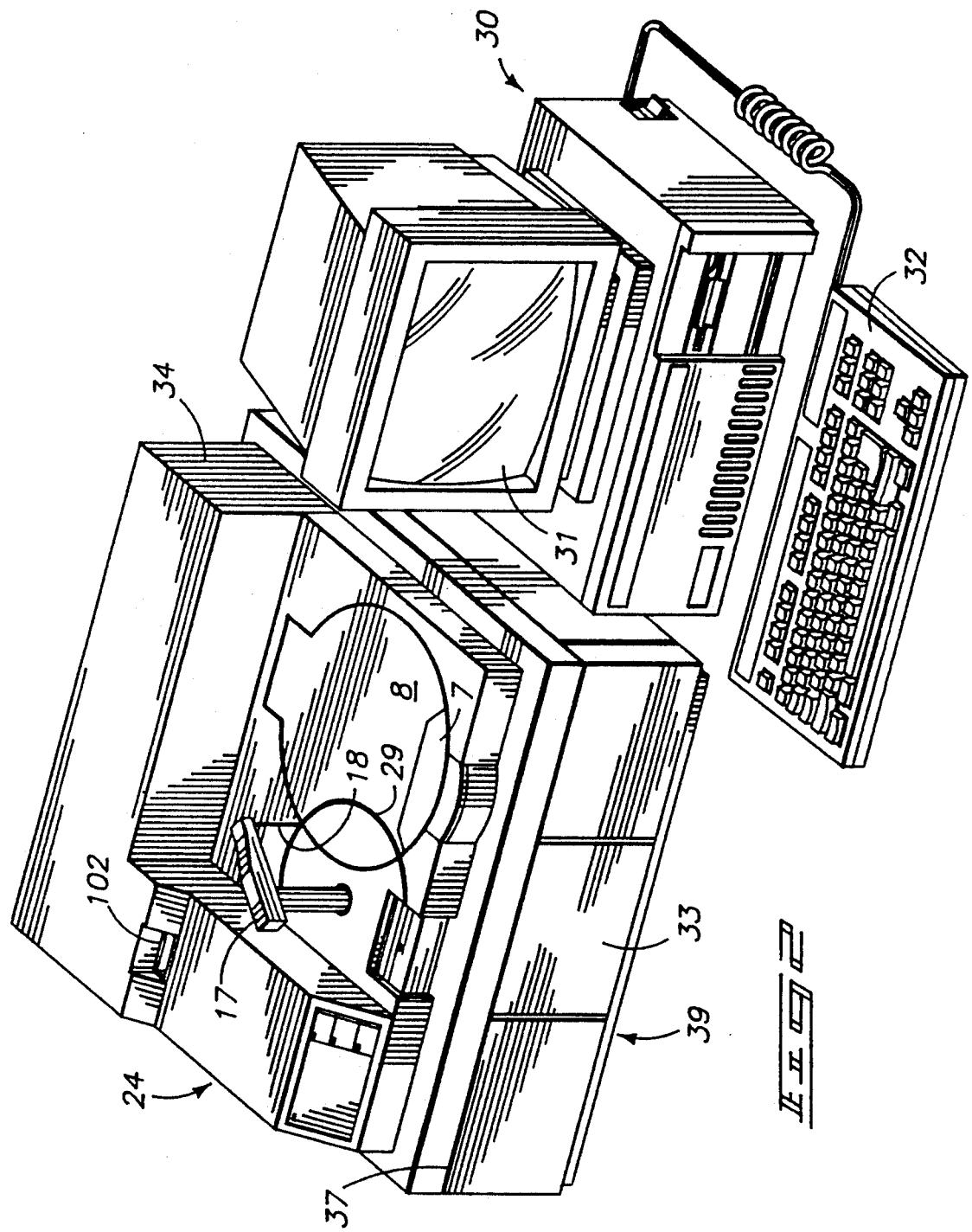
FIG. 2 is a perspective view of the analyzer.

The principal modular components of the chemistry instrument 24 are diagrammatically illustrated in FIG. 1. The illustrated components are specifically designed for use in association with a specially designed liquid cuvette 10.

A computerized operator interface to the chemistry instrument 24 is provided through connections to the programmable workstation 30. Most of the operator interactions with the analyzer take place at workstation 30. It is an external desktop computer located near the chemistry instrument(s) 24. It uses an industry standard operating system and bus structure, plus a hard disk. It is also provided with a custom instrument interface board for each associated chemistry instrument.

Operations required for sample testing of cuvette contents are not carried out in any predetermined sequence dictated by insertion of a sample into the chemistry instrument 24. Instead, workstation 30 serves as random access control means operably connected to the turntable 11, tray 15 and probe arm 17 for selectively transferring liquid from any container on the tray 15 to any cuvette 10 on the turntable 11 according to defined logical priority rules programmed into the workstation.

Operations carried out within the chemistry instrument 24 are timed about a repetitious cycle of operations. Each cycle involves sequentially transferring liquids to an awaiting cuvette 10 on the turntable 11, mixing the liquids, and centrifuging them for test purposes.

A monitor 31 is included within workstation 30 to display data, messages and optional menus for the operator. A keyboard 32 is included for operator input of data and instructions. A printer (not shown) of conventional design can also be provided in the system to record tests results and reports as required.

A plurality of test cuvettes 10 are releasably located within a motor-controlled turntable 11. It is powered by a DC motor 12. Motor 12 can be accurately controlled to (1) selectively index turntable 11 at a chosen angular position about its vertical axis for access to a particular cuvette and/or insertion of new cuvettes or (2) intermittently or reversibly rotate turntable 11 about its axis for mixing the contents of the cuvettes or (3) spin turntable 11 for centrifuging the contents of the cuvettes during photometric analysis.

A liquid transfer module includes a single probe arm 17 movably supported on the instrument 24 about a vertical axis. The outer end of probe arm 17 carries a downwardly extending pipette 18. Pipette 18 is used for transferring liquids between various locations about the chemistry instrument. Its lower or outer end is open for receiving or discharging liquids.

Probe arm 17 is supported and powered by a positioning assembly 19. The positioning assembly 19 has two stepper motors—one for imparting rotational motion to probe arm 17 and one for imparting vertical motion to it. Positioning assembly 19 can selectively move probe arm 17 and pipette 18 both angularly and axially relative to the vertical axis of probe arm 17.

The tip or lower end of pipette 18, while in an elevated condition permitting angular movement about the chemistry instrument 24, projects slightly into an open arcuate groove 29 (FIGS. 2,3) formed about the cover 34 of the instrument enclosure. Groove 29 is centered about the axis of probe arm 17 and is recessed within cover 34. It overlaps the bottom of pipette 18 to prevent its accidental engagement with the hands of an operator as the pipette travels from one station to the next. The protective overlap of the pipette tip eliminates the danger of accidently impaling adjacent personnel when pipette 18 is subsequently lowered.

A cuvette dispenser module 13 is arranged on the framework of the equipment in a position immediately above the turntable 11. It includes a storage magazine for a plurality of stacks of cuvettes 10. It also includes an apparatus for transferring individual cuvettes 10 from a randomly selectable stack within the magazine 75 to a receiving compartment on turntable 11. Used cuvettes 10 are discarded into a removable cuvette disposal container (not shown) as new cuvettes are delivered to the turntable 11 by operation of a reciprocating ram. The cuvette disposal container can be a bag or bin into which used cuvettes drop when ejected from turntable 11.

The optical system 14 is contained within a housing positioned next to turntable 11. Optical system 14 performs photometric tests on the contents of cuvettes 10 while they are being spun about the turntable axis. The optical system 14 measures both fluorescent emissions and light absorbance by cuvette contents within the turntable 11. Photometric test groups typically supported include routine chemistries, special proteins, therapeutic drugs, and drugs of abuse.

For absorbency tests, the optical system 14 measures radiation at 180 degrees to the incident light. Readings are made at several wavelengths on a diode array, but only those points requested in specified test parameters are processed by the instrument 24. System offsets are subtracted from the results and the sample signal is divided by a reference signal. The negative logarithm of this ratio is the absorbance.

When conducting fluorescent tests, emitted radiation at a wavelength longer than that of the source is measured at 90 degrees to the incident beam. System offsets are subtracted and the intensity is then normalized using a reference signal.

A sample/reagent tray 15 is rotatably mounted about a vertical axis parallel to and spaced from the axis of turntable 11. It is rotatably powered by a stepper motor 16. Tray 15 consists of a circular reagent bottle support surrounded by separate interlocking ring segments 26. The removable ring segments 26 are used to hold reagents and samples required for assay procedures during operation of chemistry instrument 24.

Tray 15 supports a plurality of liquid containers, namely the reagent bottles 25, open cups 35 and open wells 36. The interchangeable ring segments 26 have two alternate configurations. One includes apertures for removably supporting individual sample cups 35. The other includes a plurality of integrally molded sample wells 36.

The individually removable cups 35 serve as containers for test samples supplied to the instrument 24 by the operator within one or more cups within a ring segment 26. Wells 36 are used by the instrument components in conjunction with operation of probe arm 17 for aliquoting of samples from a draw tube and for sample dilution purposes. The probe arm 17 can selectively transfer liquids from one well 36 to a second well 36, from a cup 35 to a well 36, or from a reagent bottle 25 to a well 36.

Access to the sample/reagent tray 15 is provided by a hinged tray access cover 8 formed in the enclosure cover 34. More limited manual access to a single ring segment 26 located at the front of the chemistry instrument 24 is provided by a hinged segment access port 7, which is a sub-assembly of cover 8.

Figure 3:
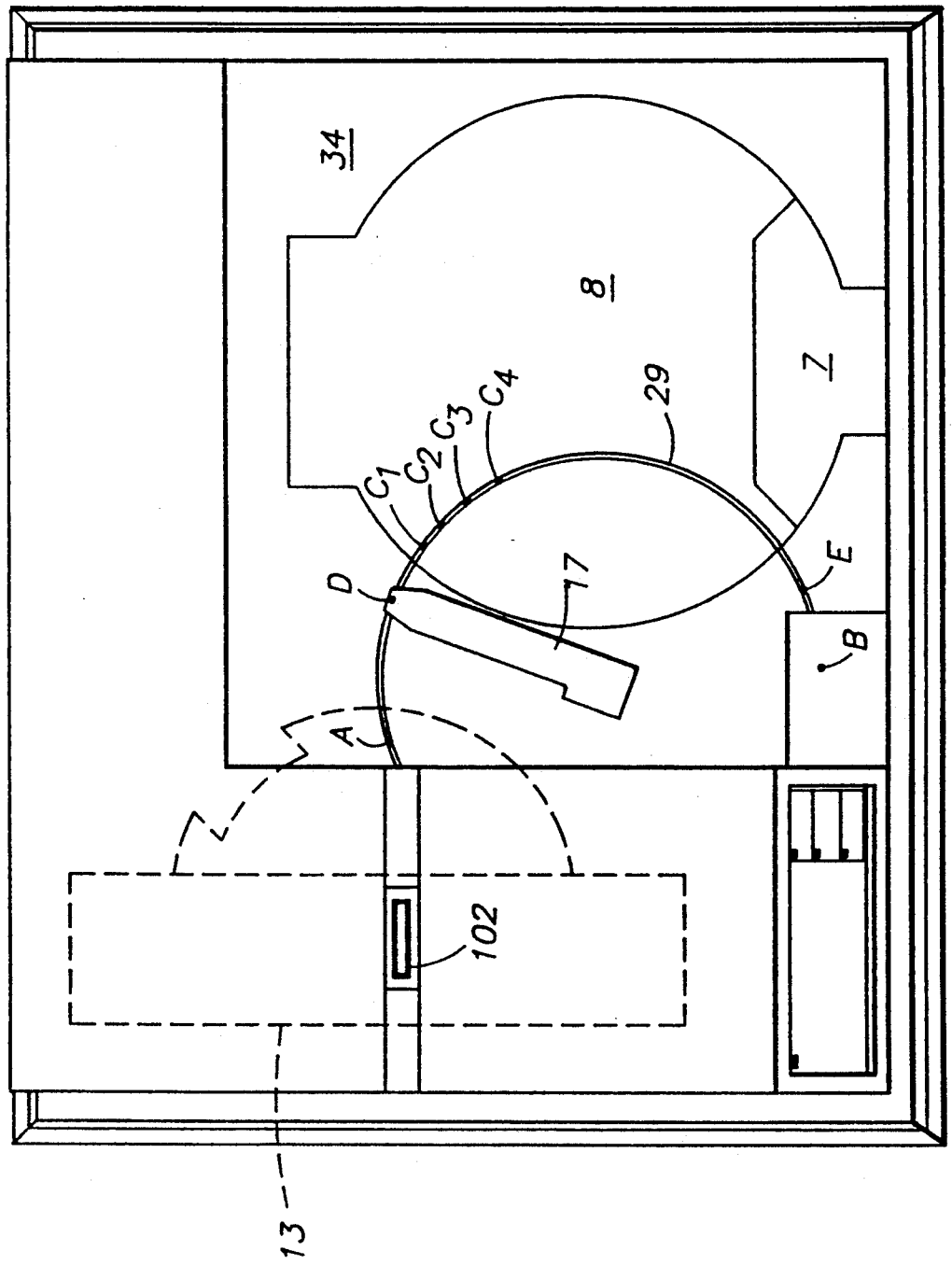
FIG. 3 is a plan view of the chemical instrument enclosure.

A stepper motor 16 can be operated to index sample/reagent tray 15 to a selected position about its axis with one or more selected containers at one of four container access stations shown in FIG. 3 at locations $C_1$, $C_2$, $C_3$, $C_4$ on the equipment framework. Each container access station intersects the path of pipette 18, which is coincident with groove 29.

Scanning means is provided next to the tray 15 for capturing identifying information from encoded indicia on a container positioned on it.

A cooling system (not shown) for the chemistry instrument 24 incorporates multiple thermoelectric cooling units. These are needed in the areas of the sample/reagent tray 15 and the turntable 11. Heat can be removed from the system by air exchange through a plurality of heat sinks.

A sample tube entry port 20 is provided on the framework for receiving and supporting successive individual draw tubes 27 as they are introduced into the instrument by the operator. Its primary use is to permit the taking of aliquots from positively identified, sealed patient draw tubes. It can also be used for delivery of control liquids from tubes of a similar exterior configuration, whether covered or open. Positive identification can be provided by an encoded label on each draw tube 27. The label is scanned by a bar code reader included within the sample tube entry port 20.

Each draw tube 27, of conventional design, is sealed by a closure at its upper end. Sample tube entry port 20 supports each manually inserted draw tube 27 while pipette 18 pierces the closure 162 to access liquid sample material from the tube interior. Liquid removal from successive tubes 27 occurs at a sample access station B along the arcuate path 29.

Puncturing means are provided within the sample tube entry port 20 for temporarily forming an opening through a closure on a manually-delivered draw tube 27 placed within it. A ram positioned below the puncturing means receives and coaxially orients a manually placed draw tube 27 relative to the puncturing means. It moves the draw tube parallel to a fourth vertical axis (centered along the puncturing means) between a lowered position wherein the draw tube 27 is clear of the puncturing means and a raised position wherein the puncturing means forms a temporary opening through the draw tube closure for subsequent coaxial insertion of the pipette 18. The interior of the draw tube 27 is then accessible by subsequently inserting pipette 18 coaxially through the puncturing means.

A wash/alignment module 21 is located at a fixed position on the framework. Its first purpose is to provide vertical basins within which the lower end surfaces of pipette 18 can be flushed clean during or after liquid transfer cycles. It also supports a conductive sensing plate that verifies both the radial alignment and elevational position of pipette 18 about the pipette axis on the probe arm 17 for monitoring alignment of the pipette. These operations occur at a wash/alignment station D along the arcuate path 29 of pipette 18.

A capacitive sensing circuit is operably connected to the pipette 18 and to conductive members located next to the tray 15 and within the sample tube entry port 20.

The sensing circuit detects the level of liquid in a container on the tray or a draw tube 27 as it is approached by the pipette.

A second analytical means, shown as an Ion Specific Electrode (ISE) module 38 of conventional design and operation, is included within the chemistry instrument 24. It is illustrated generally in FIG. 1. Potentiometric tests may be requested and run by the ISE module 38 simultaneously with photometric tests being conducted by the optical system 14.

Samples are delivered to the ISE module 38 by pipette 18 at a sample delivery station E along the arcuate path 29 (FIG. 3). Module 38 can include tests for the presence of a variety of analytes, such as sodium, potassium, chloride, lithium or calcium. For each analyte, all sample types are analyzed in the same manner. The different sample types can be loaded using different dilution factors.

The ISE module 38 consists of electrodes specific to the chosen analyte, a reference electrode and the associated fluid system required to process tested samples. The potentiometric measurement consists of a voltage difference between the analyte's electrode and the reference electrode.

Water is supplied to pipette 18 from a syringe module 22 connected to a water supply container in a container rack 28. The syringe module 22 consists of a volume displacement syringe and associated valves leading to a source of water and a waste water container (not shown). It is used for all aspirations of samples, reagents and diluents in the chemistry instrument 24. The syringe module is of conventional design.

Tubing 23 (FIG. 1) connects syringe module 22 to pipette 18. Tubing 23 contains water that can be moved in opposite directions to receive or discharge liquids at the lower end of pipette 18.

The above components are individually operable under control of a distributed computerized controller system governed by the programmable workstation 30. Workstation 30 is electronically linked to the instrument via a bi-directional communications interface. This interface is used to communicate patient requisitions to the chemistry instrument 24 and to receive the associated test results from the instrument 24. All control functions can be randomly initiated under control of scheduling software and logic to match pending requisition requirements and current instrument status conditions.

The external computer can send patient requisitions to the workstation either individually or in ring segment groups. The workstation can send test results to the external computer.

The control system associated with chemistry instrument 24 includes several dedicated microprocessors and programmable memory devices. They individually operate the system components as prioritized by scheduling software residing in the instrument CPU board. The workstation 30 includes monitoring means for maintaining a current record of the amount of liquid in containers on the sample/reagent tray 15. Controlling software associated with the microprocessors causes the mechanical components of the chemistry instrument 24 to carry out all operations efficiently and effectively without operator intervention, using a random sequence of movements dictated by outstanding test requirements.

The arrangement of operational stations along the arcuate path of pipette 18 permits transfer of liquids from a draw tube 27 at the sample access station B to a well 36 at a container access station $C_1$ or $C_2$ on the sample/reagent tray or from a well 36 to a cuvette 10 at the cuvette access station A on turntable 11. Alternately, pipette 18 can transfer sample diluents (buffers) from the reagent bottles 25 at container access stations $C_3$ or $C_4$ on the sample/reagent tray 15 to a well 36 at a container access stations $C_1$ or $C_2$. In addition, it can transfer liquids from one well 36 to another, or from a cup 35 to a well 36 for dilution purposes at container access stations $C_1$ or $C_2$. Direct transfer of reagents from bottles 25 to cuvettes 10 can also take place at cuvette access station A. A wash or pipette alignment procedure can also be periodically accomplished at wash/alignment station D as required. ISE tests are initiated by optional delivery of sample liquids to the ISE station E.

Cuvettes

Figure 6:
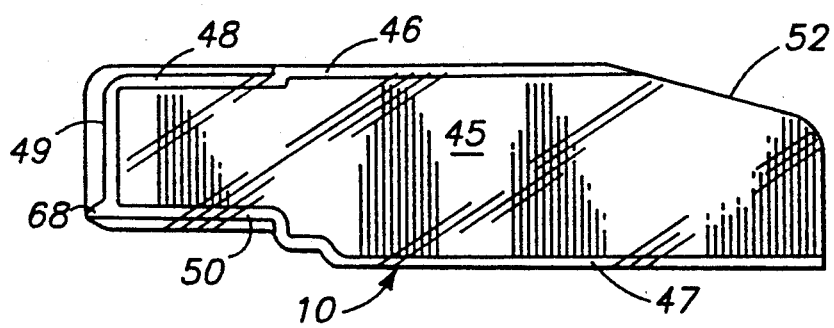
FIG. 6 is a side elevation view of a cuvette.
Figure 7:
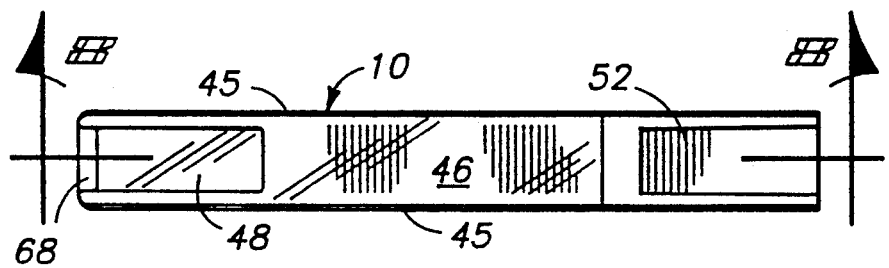
FIG. 7 is a top view.
Figure 8:
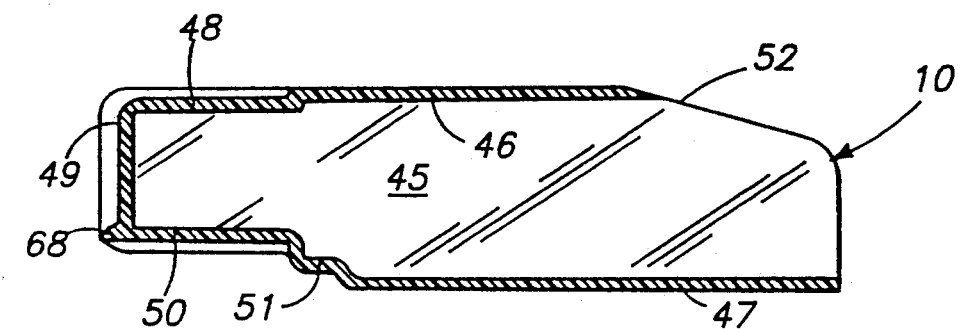
FIG. 8 is a sectional elevation view taken along line 8—8 in FIG. 7.

The disposable cuvettes 10 designed for use in turntable 11 are illustrated in detail in FIGS. 6–8. A complementary cartridge 40 for handling and storing the cuvettes is shown in FIGS. 9 and 10.

Cuvettes 10 are molded from a suitable transparent rigid plastic material that is inert to the liquids which they are to contain during use of the chemistry instrument 24. The cross-sectional configuration of each cuvette is rectangular. Each cuvette 10 includes parallel spaced side walls 45 joined by parallel spaced top and bottom walls 46 and 47.

One end of each cuvette 10, termed its "upper end", includes an opening 52 that extends between the side walls 45. Opening 52 provides access to the interior of cuvette 10 for receipt of liquids during use of the cuvette. The edges of side walls 45 that form the opening 52 includes an angular section that assumes a horizontal orientation when positioned in turntable 11 (FIG. 12) and end edges that are perpendicular to the top and bottom walls 46 and 47. In the case of cuvettes that are pre-loaded with reagents or other materials prior to usage in the chemistry instrument 24, opening 52 can optionally be sealed by a suitable film or other cover (not shown) capable of being pierced by the descending tip of pipette 18.

The opposite end of each cuvette 10, termed its "lower end", includes perpendicular optical surfaces for transmission of light in conjunction with operation of the optical system 14. These surfaces comprise upper, end and lower optical surfaces 48, 49 and 50, respectively. Each is slightly recessed inwardly from the outer edges of side walls 45 to protect their optical surfaces from abrasion or contact during handling.

The lower end of each cuvette 10 also is provided with a transverse protruding wall 68 extending across the two side walls 45. Wall 68 provides a continuous transverse surface for abutment of the upper end of an adjacent cuvette 10 when one cuvette pushes another into position within turntable 11.

A small downwardly-facing recess 51 is provided within the bottom wall 47 of each cuvette 10 adjacent to the inner end of lower optical surface 50. The recess 51 is adapted to receive a movable detent (see FIG. 12) that yieldably holds cuvette 10 within a receiving compartment on the turntable 11.

Figure 18:
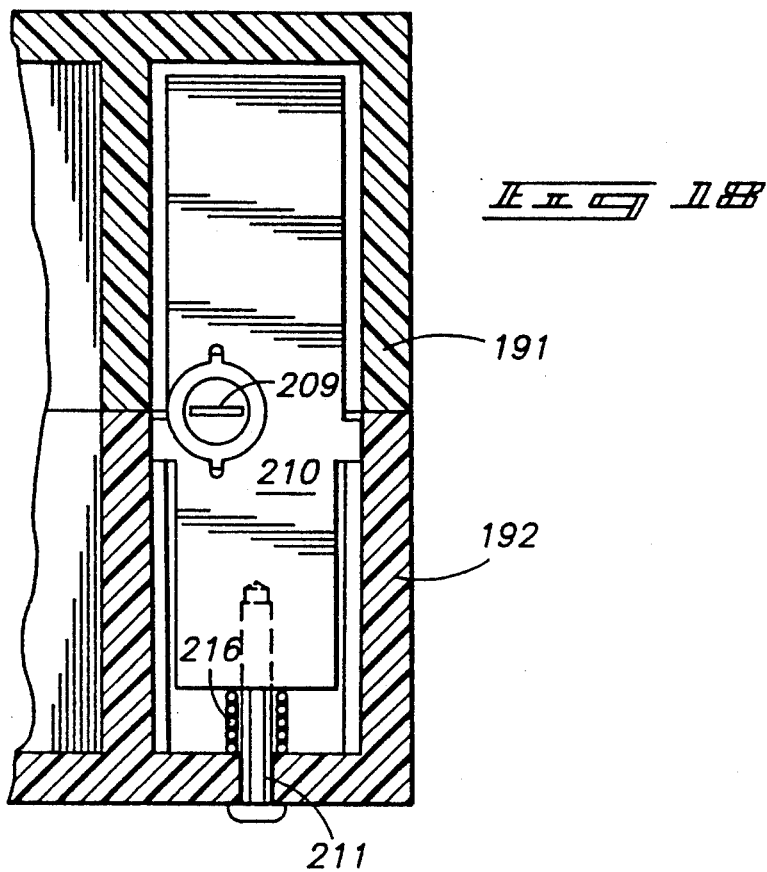
FIG. 18 is an enlarged fragmentary sectional view taken along line 18—18 in FIG. 16.

The parallel cuvettes 10 face oppositely at the respective ends of a cartridge 40 designed for insertion into the receiving cuvette magazine 75 detailed in FIG. 18. The cuvette cartridge 40 is formed from a C-shaped channel 41 having interior surfaces complementary to the exterior shape and size of the individual cuvettes 10. Cartridge 40 can be formed from any suitable stiff, resilient plastic sheet or can be extruded in the shape generally illustrated in FIGS. 9 and 10. Its purpose is to facilitate handling and storage of the large quantities of cuvettes 10 required by each chemistry instrument 24 and to expedite manual entry of cuvettes 10 into the storage magazine 75.

Cuvettes 10 fit transversely within the elongated channel 41 in abutting parallel positions within two groups. Each group of cuvettes 10 at the respective ends of cartridge 40 equals a full stack of cuvettes within the receiving magazine 75 as described below. Two pairs of inwardly bent stops 42 near the center of cartridge 40 limit inward motion of cuvettes along the length of the magazine. Outward movement of cuvettes at each end of the cartridge 40 is resisted by smaller end stops 43 bent inwardly in the path of cuvettes 10 as they exit the cartridge 40.

Turntable

Turntable 11 is generally detailed in FIGS. 11–13. It comprises a circular, radially-slotted wheel rotatably mounted about a vertical axis X—X (FIG. 13). The outer periphery of the turntable 11 presents a series of equiangularly spaced radial compartments 53. Each compartment 53 individually receives a cuvette 10 in the manner shown in FIG. 12.

Each compartment 53 comprises a radial slot having an interior cross-sectional shape and size that is complementary to the exterior cross-sectional shape and size of a cuvette 10. The compartments 53 are arranged about turntable 11 at an oblique angle such that the angular upper edge of each cuvette opening will be oriented horizontally and perpendicular to the axis X—X (see FIG. 12). The oblique nature of each compartment also positions the optical end of each cuvette 10 at a lower elevation than opening 52 so that the liquids will be contained within each cuvette without spilling, even when the turntable 11 is stationary.

An axial slot 54 intersects each compartment 53 across its outer end. Slots 54 extend through the upper and lower surfaces of the turntable 11. They provide light access to the optical surfaces 48–50 of cuvettes 10. Slots 54 permit passage of light through the individual cuvettes 10 and are used in conjunction with operation of the optical system 14 to facilitate photometric testing of cuvette contents while within the turntable 11.

The cuvettes are yieldably held within the radial compartments 53 by spring 55 (FIGS. 12, 13). The outer ends 61 of the longitudinal springs 55 are enlarged to enable them to fit within the recesses 51 formed in the cuvettes 10. The spring ends 61 constitute yieldable detents that radially limit outward movement of each cuvette 10 relative to the turntable 11.

Springs 55 also serve as interior supports within compartments 53. They yieldably maintain the top walls 46 of cuvettes 10 in engagement with the upper inside surfaces of the compartments 53. The cover 59 about turntable 11 is fabricated of an electrically conductive plastic material. Springs 55 maintain firm surface-to-surface contact between the top wall 46 of each cuvette 10 and the interior surface of cover 59. This provides effective heat transfer to each cuvette to minimize the time required to warm it in preparation for receipt of a test sample. The cover 59 can be heated as the turntable 11 is rotated, using recirculated air from an adjacent stationary source of controlled heat (not shown).

Cuvettes 10 held within the turntable 11 are individually accessible and open for reception of samples and reagents as required by requisitioned assays. Liquids are introduced through the openings 52 of the respective cuvettes 10 by operation of probe arm 17 and pipette 18 at the previously-identified cuvette access station A. All incubation of samples involved in an assay occurs within cuvettes 10 in the turntable 11.

The upper surface of the supporting central plate 56 on turntable 11 is provided with a plurality of tapered radial guide surfaces 57. Surfaces 57 are centered between each radial compartment 53 and are obliquely aligned with the respective compartments 53. They are utilized to accurately index turntable 11 during reception of incoming cuvettes, as will be described in conjunction with the interaction between the cuvette dispenser module 13 and turntable 11.

As can be seen in FIG. 12, the turntable 11 holds cuvettes 10 in elevationally tilted radial positions with their openings 52 exposed for reception of liquid materials. At the same time, their optical surfaces 48, 49 and 50 are exposed through slots 54 for transmission of light as required by operation of optical system 14.

Turntable 11 is rotatably supported about a stationary vertical shaft 62 (FIG. 13) fixed to the supporting framework of the chemistry instrument 24. It is rotated by peripheral gear teeth 63 that are drivingly engaged with a motor-driven gear (not shown) operatively powered by motor 12.

Indexing of turntable 11 is accomplished by a circular slotted rim 60 that rotates between a light sensor 74 on the framework of the chemistry instrument. A rotational "home" position is defined by a depending flag 129 and a second sensor 139.

Optical Test System

FIGS. 14–20 illustrate the physical arrangement of the components that make up optical system 14, which is located directly adjacent to turntable 11. FIG. 21 is a diagrammatic view showing the light paths involved in providing electronic measurement of absorbance as a function of light transmitted through the test samples in the individual rotating cuvettes 10 or fluorescence polarization as a function of emissions produced by test samples within individual cuvettes 10 in response to light excitation.

Figure 15:
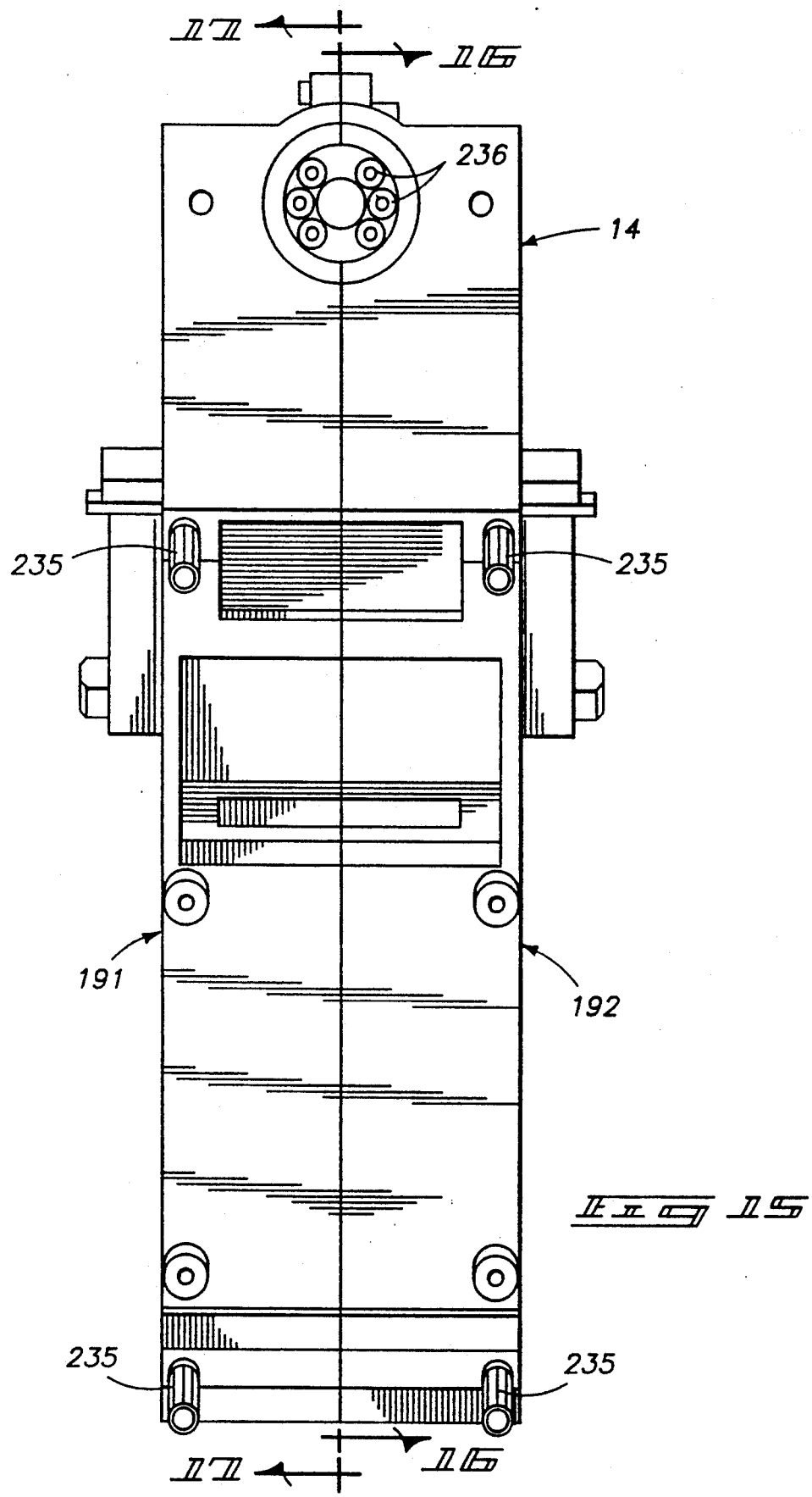
FIG. 15 is a front view of the enclosure as viewed from the left in FIG. 14.
Figure 16:
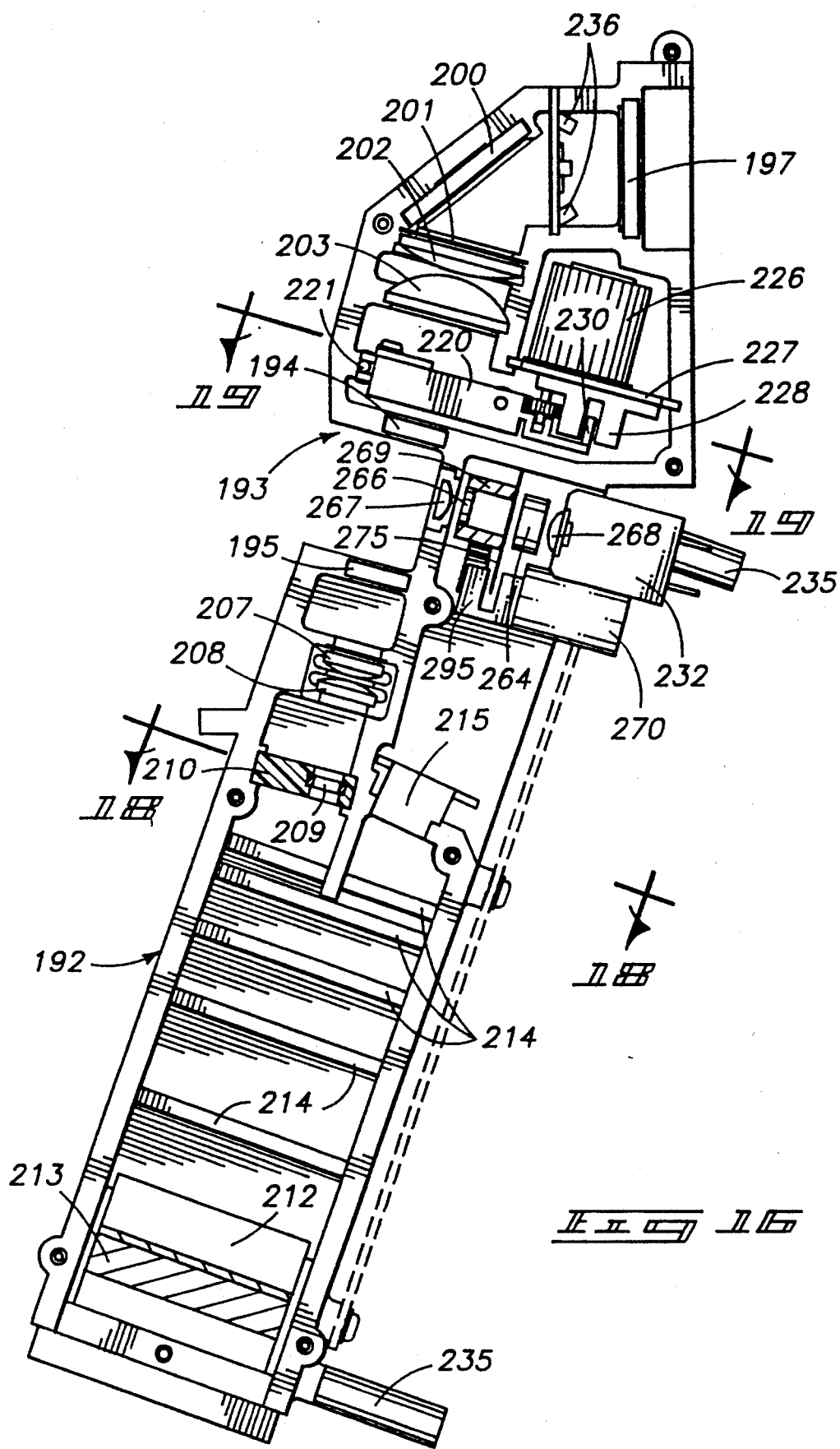
FIG. 16 is a sectional view of the right hand side of the optical system module as seen along line 16—16 in FIG. 15.
Figure 17:
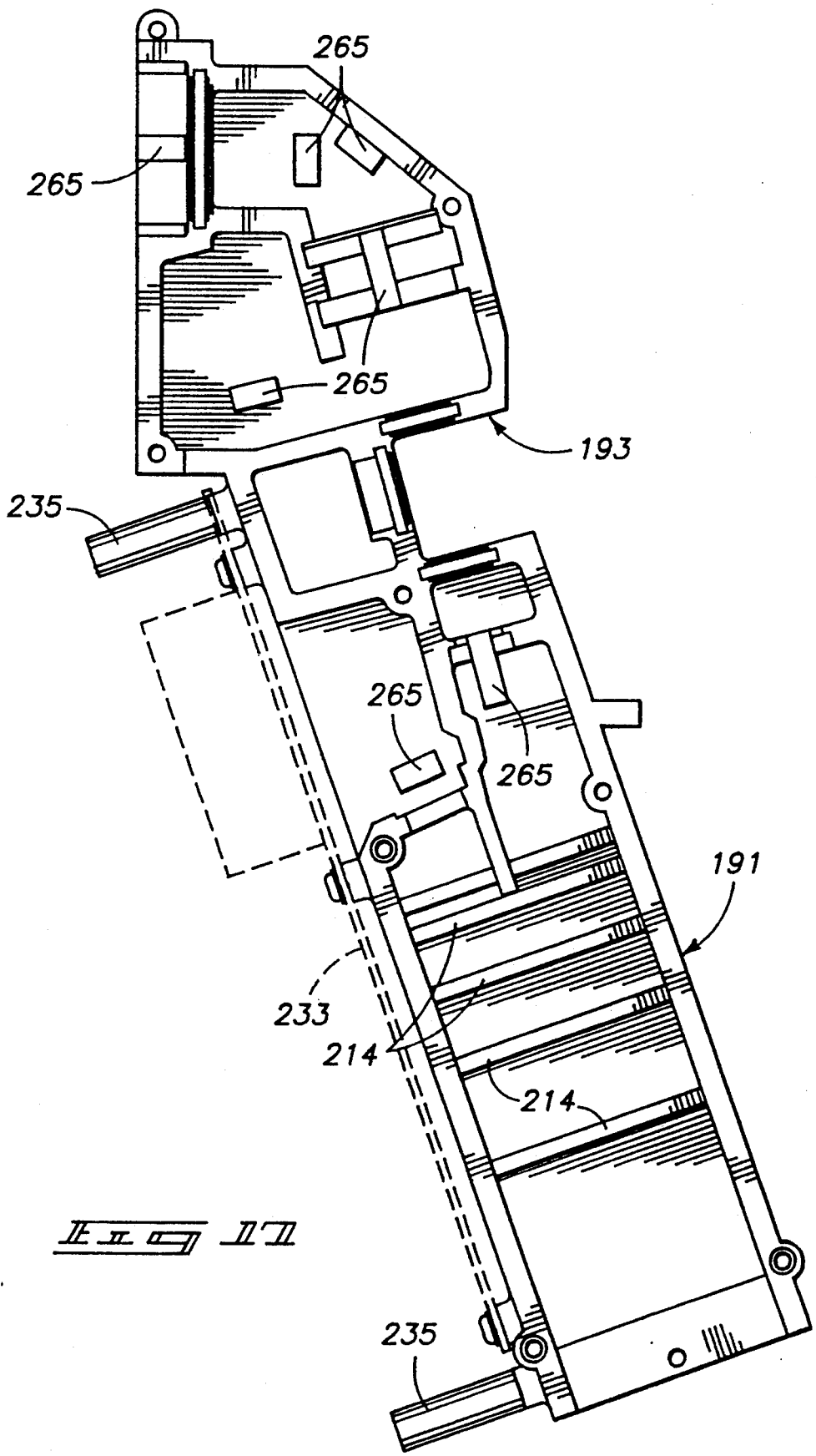
FIG. 17 is a sectional view of the left hand side of the optical system module as seen along line 17—17 in FIG. 15.

The optical system is located within a molded lightproof enclosure assembled from complementary left and right compartments 191 and 192, as shown in FIG. 15. The interiors of compartments 191 and 192 are illustrated in FIGS. 16 and 17, respectively.

Figure 4:
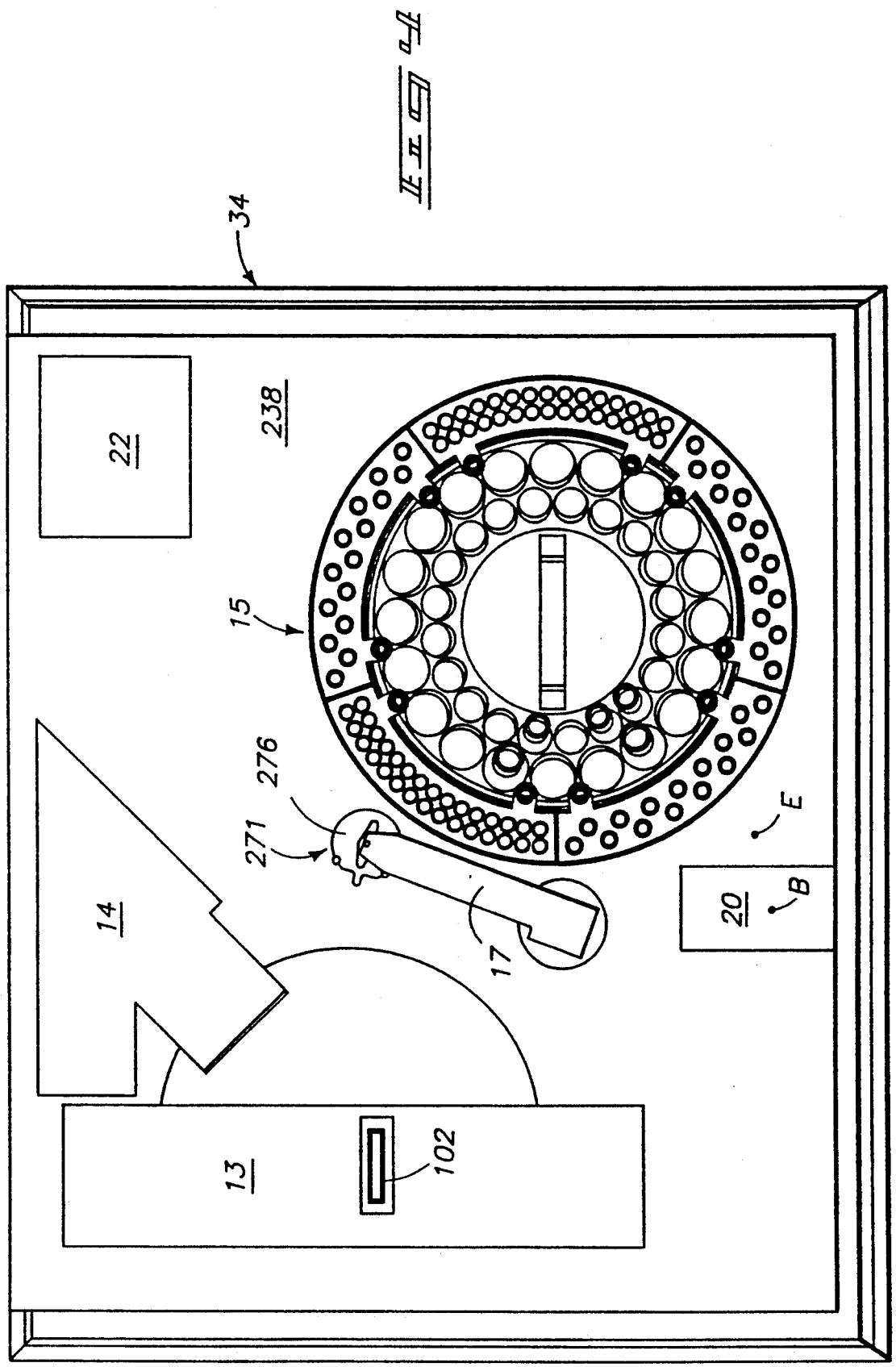
FIG. 4 is a plan view of the chemical instrument enclosure with the cover removed.
Figure 5:
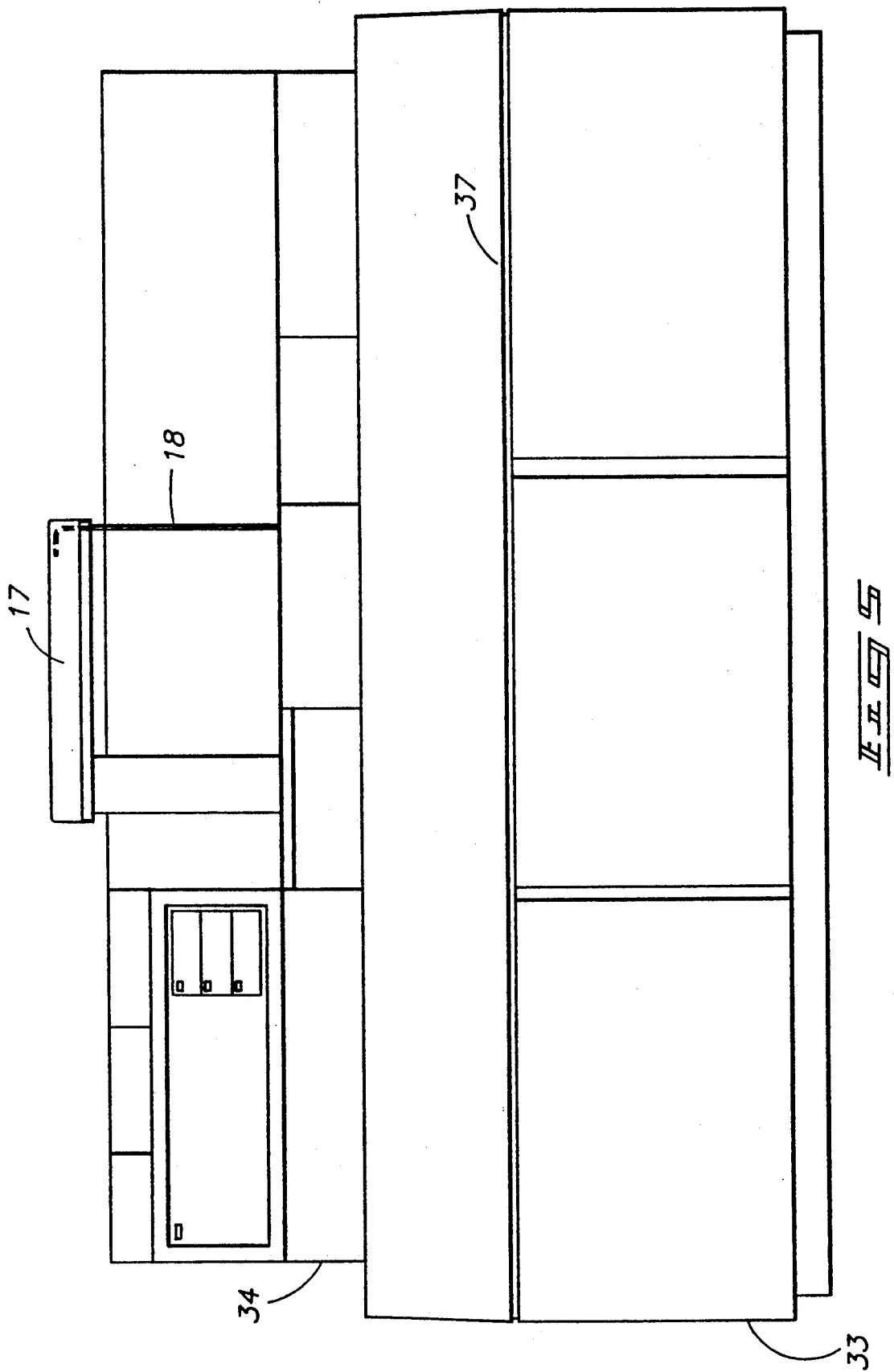
FIG. 5 is a front elevation view of the enclosure.

The exterior of the enclosure includes a transverse recess 193 that extends fully across the widths of the two joined compartments 191, 192. The outer periphery of turntable 11 is positioned to rotate through recess 193. The position of turntable 11 with respect to the optical system 14 is generally shown in FIG. 4 and is more specifically illustrated in dashed lines in FIG. 14.

The inclined orientation of recess 193 complements the inclined arrangement of the cuvettes 10 about the periphery of turntable 11. Recess 193 within the optical system enclosure overlaps the previously-described slots 54 in turntable 11 which provide exterior exposure to optical surfaces 48, 49 and 50 at the lower end of each cuvette 10.

Recess 193 is provided with an upper light window 194, an opposed lower light window 195 and an end light-collecting lens 267. Windows 194 and 195 permit transmission of light through the upper and lower optical surfaces 48, 50 of each cuvette 10 for absorbance tests. Lens 267 collects fluorescent light emissions from within each cuvette 10 through its end optical surface 49.

A conventional pulsed Xenon lamp 190 is used in the optical system 14 as an intermittent high intensity light source for both absorbance and fluorescence polarization testing purposes. Its excitation is timed to coincide with the time of passage of each cuvette 10 through the recess 193. A lamp power supply 188, also of conventional design, is included in the chemistry instrument 24 to provide required electrical power to the lamp 190.

For illustrative purposes, FIGS. 16 and 17 show the optical elements (primarily lenses and filters) within compartment 192 only. They are located along the parting line separating the two compartments and actually project transversely into both compartments.

The right compartment 192 is illustrated in the disassembled view shown at FIG. 16. Each optical element is accurately positioned within the enclosure by engagement against a complementary control surface presented within compartment 192. The molded control surfaces, that complement the peripheral exterior of the respective optical elements, locate them along the length of the light path leading from lamp 190. Each lens is axially biased against the engaged control surfaces by surrounding flexible tubing, which is slightly compressed behind the lens to assure its proper positioning within the enclosure.

Left compartment 191 shown in FIG. 17, includes complementary recesses and mountings for these elements, which are situated along the tongue and groove seal between the two compartments 191, 192. The mountings include resilient foam pads 265 which transversely engage the optical elements. The pads 265 within compartment 191 serve as complementary retaining surfaces that act in structural opposition to the control surfaces within compartment 192 for maintaining the optical elements in a centered position across the parting line when the two compartments are assembled.

The optical system will be described first with respect to the absorbance subsystem used for detecting transmission of different light wavelength during analysis of reaction mixtures within cuvettes 10.

Light pulses from lamp 190 pass through a circular window 197. The resulting light path is surrounded by a ring of reference diodes 236 that measures incoming light intensity. The path of the light entering the optical system enclosure is then turned by a diagonally placed mirror 200. This first light path leads to a first detector 215 for monitoring the intensity of light absorbed by a test sample within a cuvette 10 in response to light passing along the first light path through the pair of optical surfaces 48, 50 at the top and bottom of the cuvette.

Light from lamp 190 is initially focused across the center plane of each cuvette 10 located within recess 193 by two plano-convex lenses 202 and 203 provided in the upper optics module shown in FIG. 16. A large lens aperture 201 is located directly adjacent to lens 202 and restricts the passage of light to a defined circular aperture area.

Light passing through the cuvettes 10 within recess 193 is again focused at a transverse slit aperture 209. The required focusing is accomplished by use of paired plano-convex lenses 207 and 208 in the lower optics module shown in FIG. 16.

Details of the mounting arrangement for slit aperture 209 are shown in FIG. 18. The slit aperture 209 is mounted within a supporting block 210 slidably carried within the enclosure for adjustment in a direction perpendicular to the length of the slit aperture 209. Adjustment of block 210 is accomplished through a screw 211 acting in opposition to a surrounding compression spring 216.

The narrow, focused beam of light that passes through slit aperture 209 is directed to a holographic grating 212 supported on a mounting block 213 within the interior of the enclosure. The holographic grating 212 is positioned at an angle to the axis of the light beam (see FIG. 20) to direct resulting component light wavelengths onto a photo diode array 215 capable of spatially detecting the intensities of light at a plurality of discrete wave lengths. The photo diode array 215 comprises a linear pattern of light-receiving diodes arranged across the enclosure at the locations where the monitored wavelengths will be diffracted by holographic grating 212.

Figure 20:
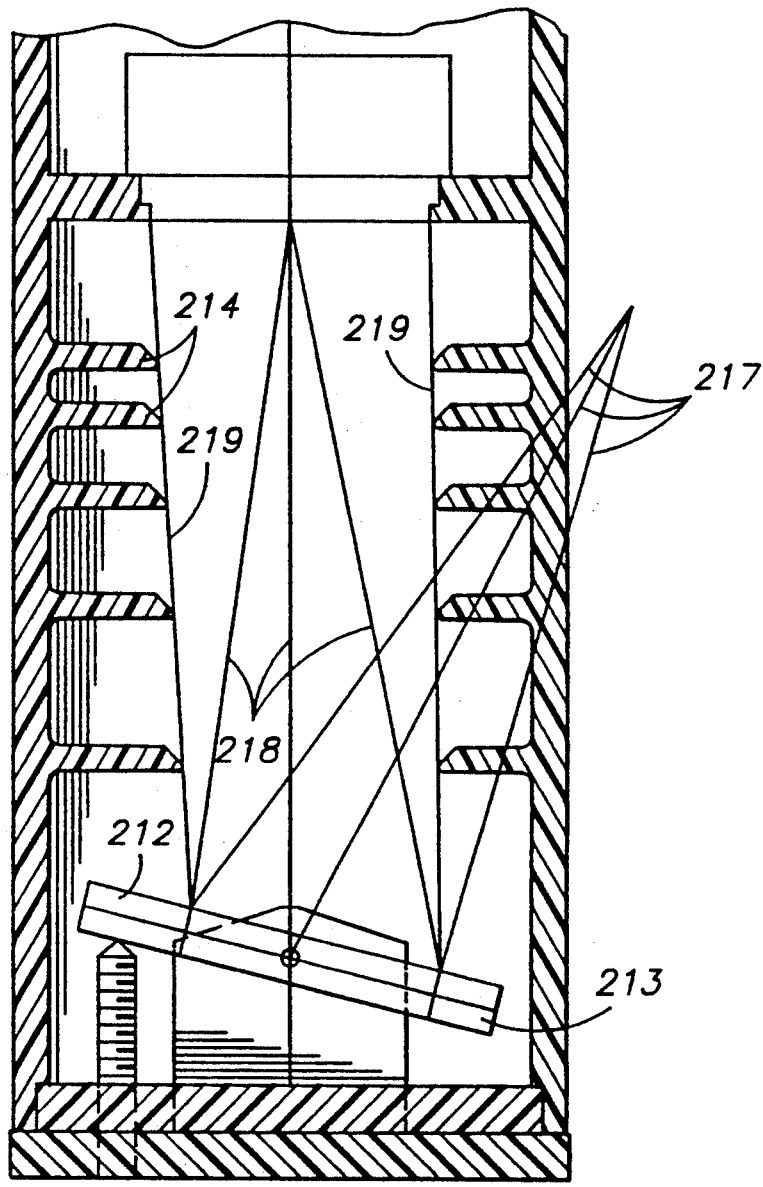
FIG. 20 is an enlarged sectional view taken along line 20—20 in FIG. 14.
Figure 21:
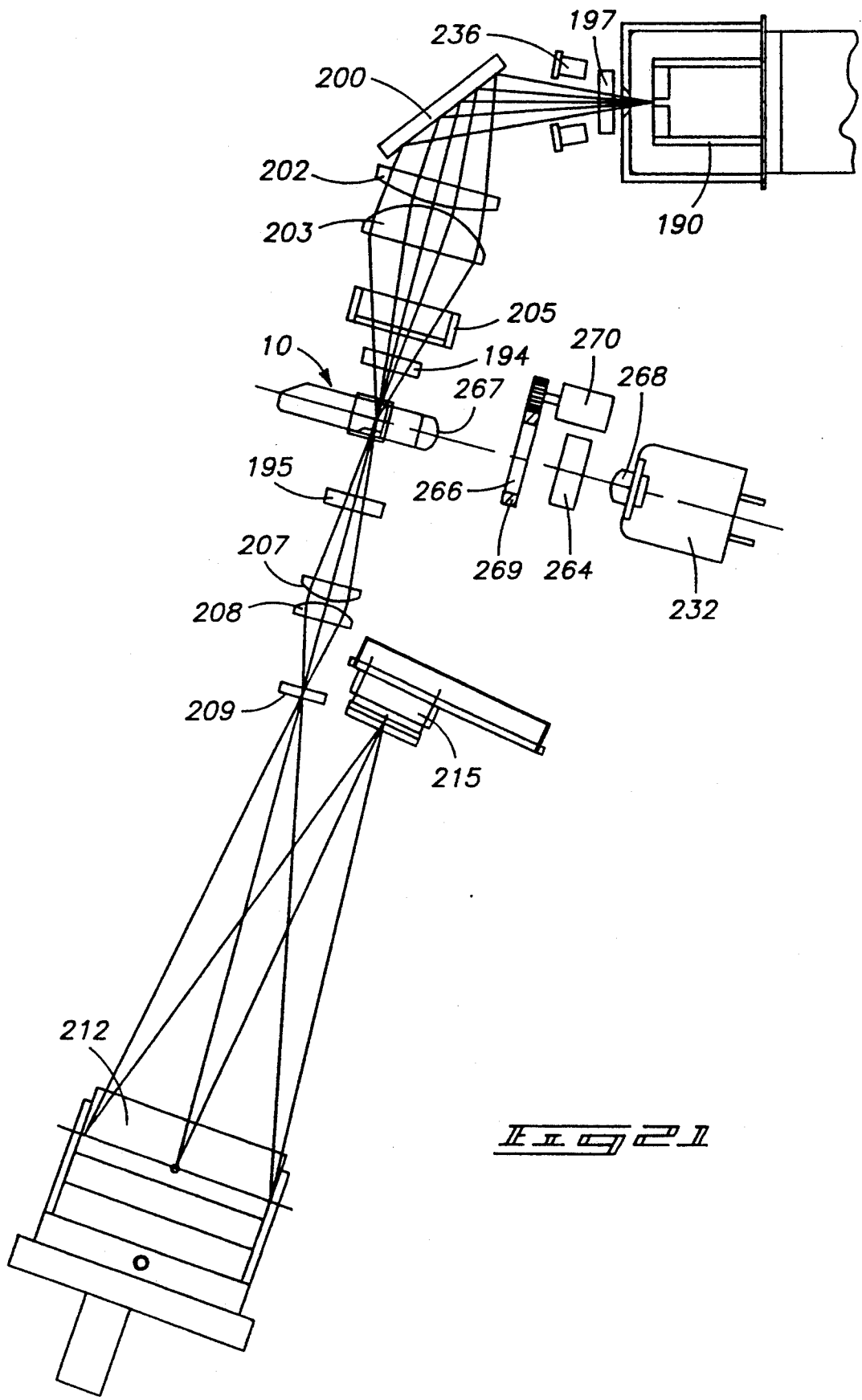
FIG. 21 is a diagrammatic view illustrating operation of the optical system.

Transverse baffles 214 are provided across the inner walls of the enclosure compartments 191, 192 to capture white light reflected by holographic grating 212, as generally indicated by lines 217 in FIG. 20. Lines 218 in FIG. 20 illustrate the beam of incoming light directed to the holographic grating 212. Lines 219, bounded by the baffles 214, indicate the width of the reflected beam directed onto the photo diode array 215.

Fluorescence polarization is monitored by use of a second detector aligned along a second light path perpendicular to the first light path and adapted to perpendicularly intersect the third or end optical surface 49 of a cuvette.

To measure fluorescence polarization that results from light excitation of the cuvette contents, a fluorescence excitation filter 205 with a polarized film mounted before it must be inserted between lamp 190 and the cuvettes 10 in turntable 11. The mounting of filter 205 within the optical system enclosure is detailed in FIG. 19.

Filter 205 is carried within a movable plate 220 guided by fixed rods 221. The rods 221 are respectively received within aligned apertures 222 formed through plate 220 and paired guides 223 that project laterally at one of its side edges. The position of plate 220 within the enclosure is controlled by a rack 224 formed on it, which is engaged by a driving gear 225. Gear 225 is powered by a motor 226 located within the enclosure.

The operation of motor 226 is controlled by electronic devices on a printed circuitboard 227. These devices include upper and lower optical cells 228, 229 that respectively detect the position of upper and lower tabs 230, 231 formed as projections from the plate 220.

Figure 19:
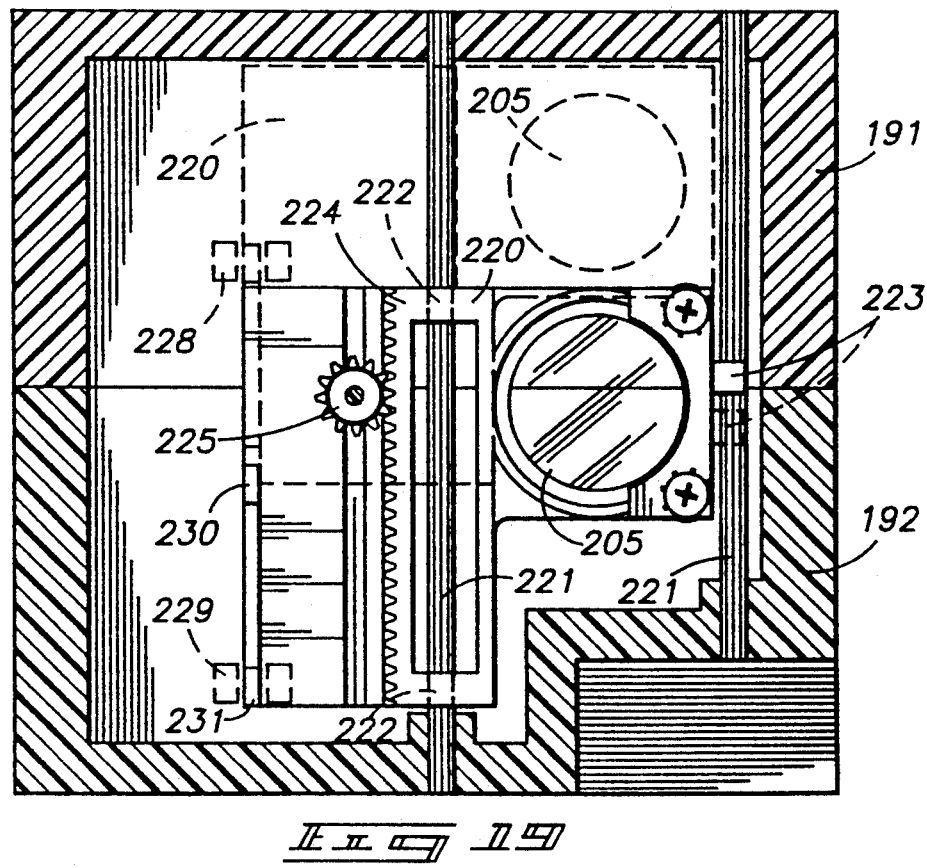
FIG. 19 is an enlarged fragmentary sectional view taken along line 19—19 in FIG. 16.

The two positions of plate 220 are shown in FIG. 19. Its lower position, situated in the light path passing through the enclosure, is used for fluorescence polarization testing purposes. Its raised position (shown in dashed lines) is utilized to remove the excitation filter 205 from within the direct light path through a cuvette 10 during absorbance tests.

The monitoring of fluorescence polarization requires measurement of emitted fluorescence at two different orientations. This can be effectively accomplished by use of the well-known arrangement of passing the fluoresced light through a polarizer to a detector and measuring one component, and then rotating the polarizer 90° and measuring the second component.

As shown in FIGS. 16 and 21, the apparatus used for monitoring intensity of fluorescence polarization includes a rotatable polarizer 266 and a fluorescence emission filter 264 coaxially aligned along a second light path leading to a receiving photo-multiplier tube 232 that produces a signal indicative of the intensity of the received fluorescence at each of the selected angular orientations. Conventional lenses 267 and 268 intensify and focus the emitted light passing through the polarizer 266 and filter 264.

The polarizer 266 is held within a supporting rotatable drum 269 having an external gear driven by a motor 270. Idler gears can be interposed between the motor 270 and the exterior of drum 269 as required.

Drum 269 is turned about its axis between two angular stops that physically limit its rotation to 90°. As one example, the drum 269 might be slotted about 90° of its periphery and a pin projecting into the slot would define the limits of its rotational motion about its central longitudinal axis. The rotational position of drum 269 is monitored by means of a timing disk 275 projecting radially outward from it. The periphery of disk 275 passes between sensors 295 (FIG. 16) to provide electrical signals as a function of the angular position of disk 275 and drum 269.

The components used for monitoring of fluorescence polarization are housed within a separate module removable from the exterior of the assembled enclosure. The exterior of the enclosure also includes support posts 235 for additional printed circuitboards (FIG. 14) that mount electronic devices associated with the optical analyzing system.

FIG. 21 graphically illustrates the path of light through the optical system. The single unit can be readily converted from an absorbance system to a fluorescence polarization system by operation of motor 226 to either place the excitation filter 205 within or outside the light beam pulsed into the enclosure by operation of lamp 190. In operation, it is anticipated that both absorbance and fluorescence polarization readings will be taken of samples within selected cuvettes 10 in the turntable 11 during each of its operational cycles. The actual nature of the tests conducted will depend upon the analytical results required by any particular tests being carried out during each turntable cycle.

Overview of Method

The method for operating the chemistry analyzer 24 basically entails a number of randomly selectable steps. Operation of the chemistry instrument 24 is timed about a repetitious sequence of cyclically transferring liquid from any selected container on the sample/reagent tray 15 to any selected cuvette 10 on the turntable 11, mixing liquids within the cuvettes on the turntable by turning it about the first axis, and rotating the turntable about the first axis. The timing of these steps are graphically depicted in FIG. 12.

The operational cycles of all components are timed to a repetitious cycle of operation of turntable 11. The turntable 11 is held stationary by motor 12 for a period during which a disposable cuvettes 10 can be delivered to the turntable 11 by operation of the cuvette delivery module. This in turn displaces a spent cuvette, which is directed into a disposal container in the instrument. The turntable 11 is sequentially indexed to a stationary angular position about the first axis indicated at X—X (FIG. 13) with a selected cuvette 10 positioned at a cuvette access station A. It is then turned about the axis while mixing or centrifuging the contents of cuvettes 10 mounted to it.

As the contents of cuvettes 10 are being centrifuged within turntable 11, the step of analyzing their contents at a location adjacent to the turntable takes place within the optical system. Following fluorescence polarization tests, the mechanically movable filter 205 is repositioned and data is transmitted from the optical testing module while turntable 11 is stationary.

Liquid samples and reagents are supplied to turntable 11 by indexing the sample/reagent tray 15 about a second axis parallel to and spaced from the first axis to a stationary angular position with a selected container positioned at a container access station C. By moving probe arm 17 and pipette 18 along an arcuate path centered about a third axis that is parallel to the first axis and intersecting both the cuvette access station A and the container access station C, the chemistry instrument 24 can selectively transfer liquids from containers positioned on the tray 15 at the container access station C to cuvettes 10 positioned on the turntable 11 at the cuvette access station A. The workstation 30 is programmed so that the step of moving the pipette 18 provides randomly accessible transfer of liquid from any container on the tray to any cuvette on the turntable in the time in which the turntable 11 is stationary during each cycle of operation.

In compliance with the statute, the invention has been described in language more or less specific as to methodical features. It is to be understood, however, that the invention is not limited to the specific features described, since the means herein disclosed comprise preferred forms of putting the invention into effect. The invention is, therefore, claimed in any of its forms or modifications within the proper scope of the appended claims appropriately interpreted in accordance with the doctrine of equivalents.

We claim:

1. An optical test apparatus for a chemical analyzer having test samples within cuvettes, comprising:

a light source located at one side of a sample location;

light directing means located between the light source and the sample location for training light from the light source in a light path leading across the sample location;

a movable filter assembly located between the light source and the sample position, the filter assembly including an excitation filter movable between a first position clear of the light path and a second position intersected by the light path;

first detector means located in the light path at the opposite side of the sample location for monitoring the intensity of light from the light source that is absorbed by a test sample while the excitation filter is in its first position; and second detector means located adjacent to the sample location and offset from the light path for monitoring the intensity of light fluoresced by a test sample in response to light excitation while the excitation filter is in its second position;

the light directing means comprising a series of optical elements contained within an assembled light-proof enclosure formed from complementary first and second molded compartments joined across a parting line extending along the center of the light path;

the series of optical element being individually positioned within the enclosure by engagement against complementary control surfaces that are included within the first compartment and that locate the optical elements along the length of the light path; and complementary retaining surfaces presented in the second compartment in structural opposition to the control surfaces of the first compartment for maintaining the optical elements in a centered position across the parting line when the first and second compartments are assembled.

2. The optical test apparatus of claim 1, wherein the light source is a pulsed lamp.

3. The optical test apparatus of claim 1, wherein the movable filter assembly includes a polarizer;

the second detector receiving the fluoresced light through a rotatable polarizer permitting fluorescence monitoring at two angles of polarization.

4. The optical test apparatus of claim 1, wherein the excitation filter includes polarizing means for polarizing light passing through the excitation filter;

the test system further comprising:

a polarizing filter interposed between the test sample and the second detector means, the polarizing filter being rotatably mounted for monitoring light fluoresced by the test sample in two angles of polarization.

5. An optical test apparatus for a chemical analyzer for use in conjunction with a cuvette having a test sample confined between a pair of parallel spaced optical surfaces spanned at one end by a third optical surface perpendicular to the pair of parallel spaced optical surfaces, comprising:

a light source;

light directing means leading along a first light path from the light source to a test sample contained within a cuvette that perpendicularly intersects the pair of optical surfaces of a cuvette along a first light path parallel to the third optical surface, the light directing means including a excitation filter movable between a first position clear of the first light path and a second position interposed across it;

first detector means for monitoring the intensity of light absorbed by the test sample in response to light passing along the first light path through the pair of optical surfaces while the fluorescence excitation filter is in its first position; and second detector means for monitoring the intensity of light fluoresced by the test sample through the third optical surface in response to light excitation when the excitation filter is in its second position;

the light directing means comprising a series of optical elements contained within an assembled light-proof enclosure formed from complementary first and second molded compartments joined across a parting line extending along the center of the light path;

the series of optical element being individually positioned within the enclosure by engagement against complementary control surfaces that are included within the first compartment and that locate the optical elements along the length of the light path; and complementary retaining surfaces presented in the second compartment in structural opposition to the control surfaces of the first compartment for maintaining the optical elements in a centered position across the parting line when the first and second compartments are assembled.

6. The optical test apparatus of claim 5, further comprising:

a rotatable turntable holding a plurality of cuvettes about its periphery;

the light source being a pulsed lamp energized in a timed relationship to the speed of rotation of the turntable for selectively directing light to a first of the pair of optical surfaces in a selected cuvette as it intersects the first light path.

7. The optical test apparatus of claim 5, wherein the second detector means is aligned along a second light path that is perpendicular to the first light path and perpendicularly intersects the third optical surface of a cuvette.

* * * * *